(12) United States Patent
Kamisho et al.

(10) Patent No.: US 11,506,649 B2
(45) Date of Patent: Nov. 22, 2022

(54) METHOD FOR ESTIMATING HYDROGEN ABSORPTION BEHAVIOR, DEVICE FOR ESTIMATING HYDROGEN ABSORPTION BEHAVIOR, AND PROGRAM FOR ESTIMATING HYDROGEN ABSORPTION BEHAVIOR

(71) Applicant: Nippon Telegraph and Telephone Corporation, Japan (JP)

(72) Inventors: Takuya Kamisho, Musashino (JP); Masamitsu Watanabe, Musashino (JP); Takashi Miwa, Musashino (JP); Yosuke Takeuchi, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 155 days.

(21) Appl. No.: 17/053,586

(22) PCT Filed: Apr. 24, 2019

(86) PCT No.: PCT/JP2019/017469
§ 371 (c)(1),
(2) Date: Nov. 6, 2020

(87) PCT Pub. No.: WO2019/216225
PCT Pub. Date: Nov. 14, 2019

(65) Prior Publication Data
US 2021/0239674 A1 Aug. 5, 2021

(30) Foreign Application Priority Data
May 7, 2018 (JP) .............................. JP2018-089372

(51) Int. Cl.
*G01N 33/2022* (2019.01)

(52) U.S. Cl.
CPC .............................. *G01N 33/2022* (2019.01)

(58) Field of Classification Search
None
See application file for complete search history.

(56) References Cited

FOREIGN PATENT DOCUMENTS

| JP | 2004-340817 | * | 12/2004 |
| JP | 2016045158 | A * | 4/2016 |
| JP | 2016057163 | A * | 4/2016 |

OTHER PUBLICATIONS

International Search Report dated Aug. 6, 2019, issued in PCT Application No. PCT/JP2019/017469, filed Apr. 24, 2019.

(Continued)

*Primary Examiner* — Daniel S Larkin
(74) *Attorney, Agent, or Firm* — Workman Nydegger (57) ABSTRACT

To estimate penetration behavior of hydrogen up until hydrogen content reaches saturation even if load stress on steel is equal to or higher than threshold stress. A hydrogen penetration behavior estimation device includes a first measurement data input unit adapted to input first measurement data concerning variation of hydrogen content with time up until hydrogen content in steel-to-be-estimated reaches saturation when measurements are taken by applying such stress to the steel that no hydrogen embrittlement fracture occurs; a second measurement data input unit adapted to input second measurement data concerning variation of hydrogen content in the steel-to-be-estimated with time up until the steel fractures when measurements are taken by applying such stress to the steel that hydrogen embrittlement fracture occurs; a ratio calculation unit adapted to calculate increases in hydrogen contents in an initial stage of measurement and calculate a ratio of the second measurement data to the first measurement data in terms of increase in hydrogen content; and a saturated hydrogen content calculation unit adapted to multiply saturated hydrogen content based on the first mea- (Continued)

surement data by the ratio and designate the product as saturated hydrogen content of the steel-to-be-estimated, the saturated hydrogen content being reached upon application of such stress that hydrogen embrittlement fracture occurs.

11 Claims, 3 Drawing Sheets

(56) References Cited

OTHER PUBLICATIONS

Tetsuo Shiraga, Hydrogen Embrittlement of Steel, Materials and the Environment, vol. 60, No. 5, 2011, pp. 236-240.
Shinichi Suzuki et al., Estimation of Delayed Fracture Property of Steels, Iron and Steel, vol. 79, No. 2, 1993, pp. 227-232.
Tomoki Doshida et al., Enhanced Lattice Defect Formation Associated with Hydrogen and Hydrogen Embrittlement under Elastic Stress of a Tempered Martensitic Steel, Iron and Steel Tetsu-to-Hagane, vol. 98, No. 5, 2012, pp. 197-206.

\* cited by examiner

METHOD FOR ESTIMATING HYDROGEN ABSORPTION BEHAVIOR, DEVICE FOR ESTIMATING HYDROGEN ABSORPTION BEHAVIOR, AND PROGRAM FOR ESTIMATING HYDROGEN ABSORPTION BEHAVIOR

TECHNICAL FIELD

The present invention relates to a technique for estimating penetration behavior of hydrogen penetrating high-strength steel.

BACKGROUND ART

High-strength steel suffers ductility loss and significant strength reduction due to hydrogen penetrating into the steel. This phenomenon is called hydrogen embrittlement (Non-Patent Literature 1). The steel fractures due to hydrogen embrittlement and fracture time of the steel decreases with increases in hydrogen content in the steel (Non-Patent Literature 2).

Therefore, in predicting occurrence of hydrogen embrittlement, it is important to examine penetration behavior (saturated hydrogen content, variation of hydrogen content with time) of hydrogen penetrating the steel. For example, hydrogen penetration behavior can be examined by measuring hydrogen content in steel using thermal desorption spectroscopy (TDS) or the like.

CITATION LIST

Non-Patent Literature

Non-Patent Literature 1: Shiraga, "Hydrogen Embrittlement of Steel" Zairyo-to-Kankyo. 2011, p. 236-p. 240

Non-Patent Literature 2: Suzuki. et al., "Estimation of Delayed Fracture Property of Steels" Tetsu-to-Hagane. 1992, Vol. 79, No. 2, p. 227-p. 232

Non-Patent Literature 3: Doshida. et al., "Enhanced Lattice Defect Formation Associated with Hydrogen and Hydrogen Embrittlement under Elastic Stress of a Tempered Martensitic Steel" Tetsu-to-Hagane. 2012, Vol. 98, No. 5, p. 197-p. 206.

SUMMARY OF THE INVENTION

Technical Problem

Hydrogen penetration behavior in steel changes with the magnitude of load stress on the steel (Non-Patent Literature 3). If load stress on steel is equal to or lower than threshold stress below which the steel is not fractured by hydrogen embrittlement, by measuring hydrogen content in the steel at regular time intervals using TDS, it is possible to know penetration behavior of hydrogen up until hydrogen content reaches saturation.

However, if load stress on steel is equal to or higher than the threshold stress, the steel fractures while absorbing hydrogen and the load stress on the steel becomes 0 (zero) at the time of fracture, making it impossible to know penetration behavior of hydrogen up until hydrogen content in the steel reaches saturation.

The present invention has been made in view of the above circumstances and has an object to estimate penetration behavior of hydrogen up until hydrogen content in steel reaches saturation even if load stress on the steel is equal to or higher than the threshold stress (i.e., the stress at or above which steel is fractured by hydrogen embrittlement).

Means for Solving the Problem

To solve the above problem, according to embodiments of the invention, there is provided a hydrogen penetration behavior estimation method, for estimating penetration behavior of hydrogen that penetrates steel, the method making a computer carry out: a first step of inputting first measurement data concerning variation of hydrogen content with time up until hydrogen content in steel-to-be-estimated reaches saturation when measurements are taken by applying such stress to the steel that no fracture due to hydrogen embrittlement occurs; a second step of inputting second measurement data concerning variation of hydrogen content in the steel-to-be-estimated with time up until the steel fractures when measurements are taken by applying such stress to the steel that fracture due to hydrogen embrittlement occurs; a third step of reading the first measurement data and the second measurement data out of a storage unit, calculating increases in hydrogen contents in an initial stage of measurement using the first measurement data and the second measurement data, respectively, and calculating a ratio of the increase in the hydrogen content according to the second measurement data to the increase in the hydrogen content according to the first measurement data; and a fourth step of multiplying saturated hydrogen content based on the first measurement data by the ratio and designating a resulting product as saturated hydrogen content of the steel-to-be-estimated, the saturated hydrogen content being reached upon application of such stress that fracture due to hydrogen embrittlement occurs.

According to an example embodiment, in the hydrogen penetration behavior estimation method, the computer is further made to carry out a fifth step of calculating a hydrogen diffusion coefficient of the steel-to-be-estimated based on the variation, with time, of the hydrogen content in the steel on assumption that hydrogen diffuses in the steel, and calculating penetration behavior data concerning the hydrogen content in the steel-to-be-estimated upon application of such stress that fracture due to hydrogen embrittlement occurs, using a diffusion equation based on the hydrogen diffusion coefficient.

According to an example embodiment, in the hydrogen penetration behavior estimation method, the third step includes plotting the first measurement data and the second measurement an example embodiment data on a graph whose ordinate represents hydrogen content and whose abscissa represents one-half power of hydrogen charging time used for measurement, and calculating the ratio using slopes of respective straight lines passing through plot points in the initial stage of measurement.

According to an example embodiment, there is provided a hydrogen penetration behavior estimation device that estimates penetration behavior of hydrogen that penetrates steel, the hydrogen penetration behavior estimation device comprising: a first measurement data input unit adapted to input first measurement data concerning variation of hydrogen content with time up until hydrogen content in steel-to-be-estimated reaches saturation when measurements are taken by applying such stress to the steel that no fracture due to hydrogen embrittlement occurs; a second measurement data input unit adapted to input second measurement data concerning variation of hydrogen content in the steel-to-be-estimated with time up until the steel fractures when measurements are taken by applying such stress to the steel that fracture due to hydrogen embrittlement occurs; a ratio calculation unit adapted to read the first measurement data and the second measurement data out of a storage unit, calculate increases in hydrogen contents in an initial stage of measurement using the first measurement data and the second measurement data, respectively, and calculate a ratio of the increase in the hydrogen content according to the second measurement data to the increase in the hydrogen content according to the first measurement data; and a saturated hydrogen content calculation unit adapted to multiply saturated hydrogen content based on the first measurement data by the ratio and designate a resulting product as saturated hydrogen content of the steel-to-be-estimated, the saturated hydrogen content being reached upon application of such stress that fracture due to hydrogen embrittlement occurs.

According to an example embodiment, the hydrogen penetration behavior estimation device further comprises a hydrogen penetration behavior estimation unit adapted to calculate a hydrogen diffusion coefficient of the steel-to-be-estimated based on the variation, with time, of hydrogen content in the steel on assumption that hydrogen diffuses in the steel, and calculate penetration behavior data concerning the hydrogen content in the steel-to-be-estimated upon application of such stress that fracture due to hydrogen embrittlement occurs, using a diffusion equation based on the hydrogen diffusion coefficient.

According to an example embodiment, in the hydrogen penetration behavior estimation device, the ratio calculation unit plots the first measurement data and the second measurement data on a graph whose ordinate represents hydrogen content and whose abscissa represents one-half power of hydrogen charging time used for measurement, and calculates the ratio using slopes of respective straight lines passing through plot points in the initial stage of measurement.

According to an example embodiment, there is provided a hydrogen penetration behavior estimation program configured to make a computer function as the hydrogen penetration behavior estimation device.

Effects of the Invention

The present invention makes it possible to estimate penetration behavior of hydrogen up until hydrogen content in steel reaches saturation even if load stress on the steel is equal to or higher than the threshold stress (i.e., the stress at or above which steel is fractured by hydrogen embrittlement).

DESCRIPTION OF EMBODIMENTS

An embodiment of the present invention will be described below with reference to the drawings.

Configuration of Hydrogen Penetration Behavior Estimation Device

Figure 1:
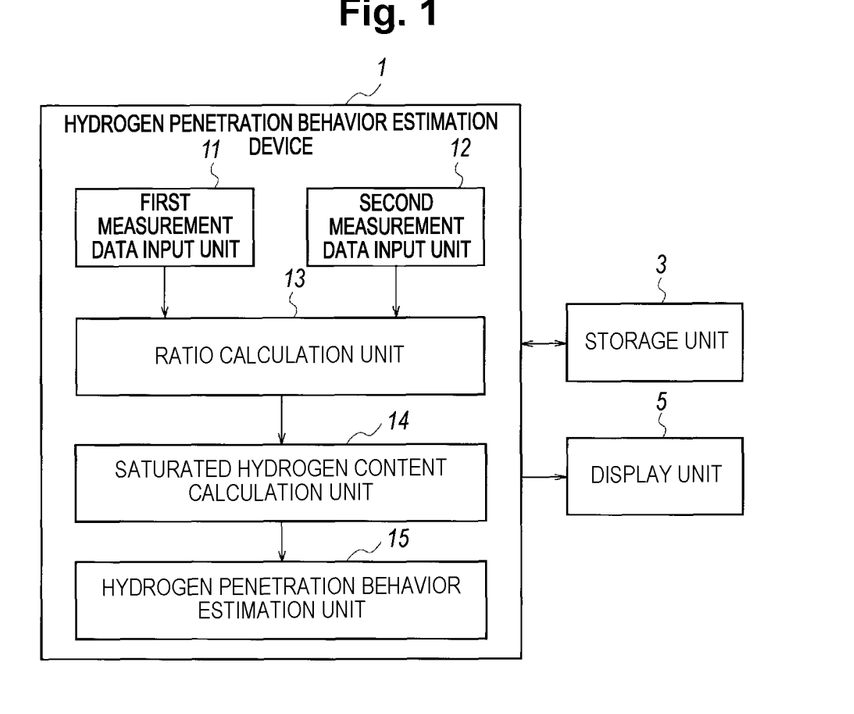
FIG. 1 is a diagram showing a configuration of a hydrogen penetration behavior estimation device.

FIG. 1 is a diagram showing a configuration of a hydrogen penetration behavior estimation device 1 according to the present embodiment. The hydrogen penetration behavior estimation device 1 includes a first measurement data input unit 11, a second measurement data input unit 12, a ratio calculation unit 13, a saturated hydrogen content calculation unit 14, and a hydrogen penetration behavior estimation unit 15. The hydrogen penetration behavior estimation device 1 is connected to a storage unit 3 and display unit 5 in a communication-ready state via its communications interface.

The first measurement data input unit 11 has a function to input first measurement data concerning variation of hydrogen content with time up until hydrogen content in high-strength steel-to-be-estimated reaches saturation when measurements are taken by applying such stress to the steel that no fracture due to hydrogen embrittlement occurs and store the second measurement data in the storage unit 3.

The second measurement data input unit 12 has a function to input second measurement data concerning variation of hydrogen content in the steel-to-be-estimated with time up until the steel fractures when measurements are taken by applying such stress to the steel that fracture due to hydrogen embrittlement occurs and store the first measurement data in the storage unit 3.

The ratio calculation unit 13 has a function to read the first measurement data and the second measurement data out of the storage unit 3, calculate increases in hydrogen contents in an initial stage of measurement using the first measurement data and the second measurement data, respectively, and calculate a ratio of the increase in the hydrogen content according to the second measurement data to the increase in the hydrogen content according to the first measurement data. The ratio calculation unit 13 has a function to plot the first measurement data and the second measurement data on a graph whose ordinate represents hydrogen content and whose abscissa represents one-half power of hydrogen charging time used for measurement, and calculate the ratio using slopes of respective straight lines passing through plot points in the initial stage of measurement.

The saturated hydrogen content calculation unit 14 has a function to multiply saturated hydrogen content based on the first measurement data by the ratio, designate a resulting product as saturated hydrogen content of the steel-to-be-estimated, the saturated hydrogen content being reached upon application of such stress that fracture due to hydrogen embrittlement occurs, and output the saturated hydrogen content of the steel-to-be-estimated to the display unit 5.

The hydrogen penetration behavior estimation unit 15 calculates a hydrogen diffusion coefficient of the steel-to-be-estimated based on the variation, with time, of hydrogen content in the steel on assumption that hydrogen diffuses in the steel. Furthermore, the hydrogen penetration behavior estimation unit 15 has a function to calculate penetration behavior data (the variation of hydrogen content with time) concerning hydrogen content in the steel-to-be-estimated upon application of such stress that fracture due to hydrogen embrittlement occurs using a diffusion equation based on the calculated hydrogen diffusion coefficient and output the penetration behavior data to the display unit 5.

Note that the saturated hydrogen content calculation unit 14 and hydrogen penetration behavior estimation unit 15, both of which handle information about hydrogen penetration behavior (saturated hydrogen content and variation of hydrogen content with time), may be implemented by a same functional part.

Operation of Hydrogen Penetration Behavior Estimation Device

Next, a hydrogen penetration behavior estimation method performed by the hydrogen penetration behavior estimation device 1 will be described. The hydrogen penetration behavior estimation device 1 performs the following steps. To estimate penetration behavior of hydrogen that penetrates steel, at least two pieces of high-strength steel of the same shape and same material are prepared in advance.

Step 1;

In step 1, variation, with time, of high-strength steel-to-be-estimated is measured until hydrogen content in the steel reaches saturation under a stress condition in which the steel does not fracture by hydrogen embrittlement. Step 1 will be described concretely below.

First, a constant-load test is conducted on high-strength steel by applying constant tensile stress to the steel while charging hydrogen into the steel. The tensile stress to be applied to the steel is, for example, 0.7 times ($0.7\sigma_b$) the tensile strength of the steel so as to be equal to or lower than threshold stress below which the steel is not fractured by hydrogen embrittlement. As a test piece of steel, for example, a smooth round bar 50 cm long and 7 mm in diameter is used. As a method for hydrogen charging, a cathodic charging method is used, where the cathodic charging method involves immersing steel in an aqueous electrolytic solution and applying a negative potential. As the aqueous electrolytic solution, 1 mol/L of an aqueous sodium bicarbonate solution is used. As an applied voltage, −1 V vs. SSE is used.

Next, when a predetermined time period elapses after the start of hydrogen charging, the steel is cut off and the hydrogen content in the steel is measured using TDS (thermal desorption spectroscopy). Under measurement conditions of TDS, for example, measurements are taken up to a temperature of 500° C. at a temperature increase rate of 10° C./min. The measurements are taken after lapses of, for example, 1 hour, 2 hours, 3 hours, 6 hours, 12 hours, 24 hours, 48 hours, and 72 hours from the start of hydrogen charging and hydrogen penetration behavior at a load stress of $0.7\sigma_b$ is examined.

Subsequently, the first measurement data input unit 11 inputs measurement data (first measurement data) on hydrogen penetration behavior taken at a load stress of $0.7\sigma_b$ and stores the measurement data in the storage unit 3.

Step 2;

In step 2, under a stress condition in which the high-strength steel-to-be-estimated is fractured by hydrogen embrittlement, the variation, with time, of hydrogen content in the steel is measured until the steel fractures. Step 2 will be described concretely below.

A stress, for example, 0.9 times ($0.9\sigma_b$) the tensile strength of the steel is applied to the steel such that the load stress applied to the steel will be equal to or higher than the threshold stress and hydrogen is charged by the same method as step 1. Before the steel is fractured by hydrogen embrittlement, for example, after lapses of 1 hour, 2 hours, and 3 hours from the start of hydrogen charging, the steel is cut off and the hydrogen content in the steel is measured using TDS.

Subsequently, the second measurement data input unit 12 inputs measurement data (second measurement data) on hydrogen penetration behavior taken at a load stress of $0.9\sigma_b$ and stores the measurement data in the storage unit 3.

Figure 2:
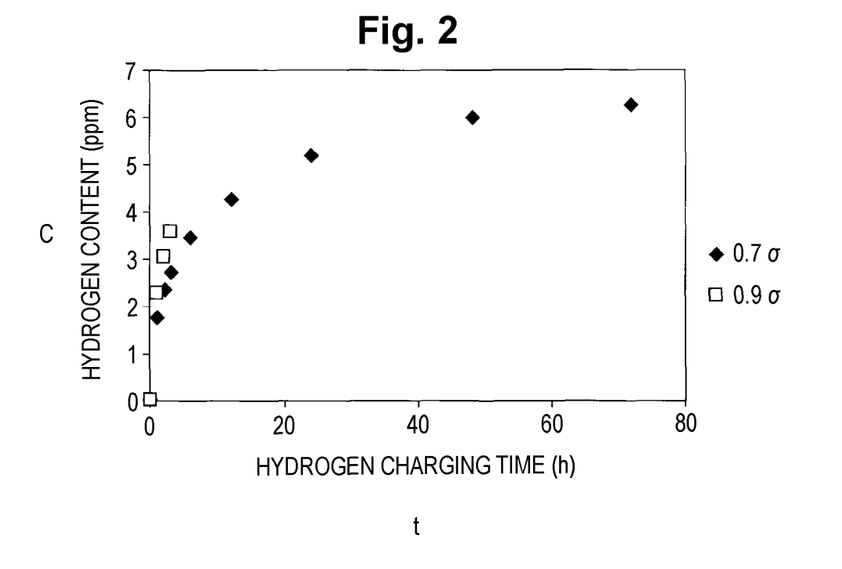
FIG. 2 is a diagram showing hydrogen penetration behavior at $0.7\sigma_b$ and $0.9\sigma_b$.

FIG. 2 is a diagram showing respective hydrogen penetration behaviors at load stresses of $0.7\sigma_b$ and $0.9\sigma_b$. The abscissa represents hydrogen charging time t and the ordinate represents hydrogen content C in the steel at the hydrogen charging time t.

Step 3;

In step 3, by plotting the first measurement data and second measurement data obtained in step 1 and step 2 on a graph whose ordinate represents the hydrogen content C and whose abscissa represents the one-half power of hydrogen charging time, a ratio between slopes is calculated. Step 3 will be described concretely below.

First, because it is thought that the hydrogen in steel penetrates inside the steel by diffusion, the hydrogen content C in steel in an initial stage of diffusion (in an initial stage of measurement) can be approximated by Formula (1). A measurer stores Formula (1) in the storage unit 3.

Formula 1

$$\frac{C}{C_s} = \frac{4}{a}\left(\frac{Dt}{\pi}\right)^{\frac{1}{2}} \quad (1)$$

where C is the hydrogen content in steel, $C_s$ is saturated hydrogen content, a is the radius of steel, D is a hydrogen diffusion coefficient, and t is hydrogen charging time.

Figure 3:
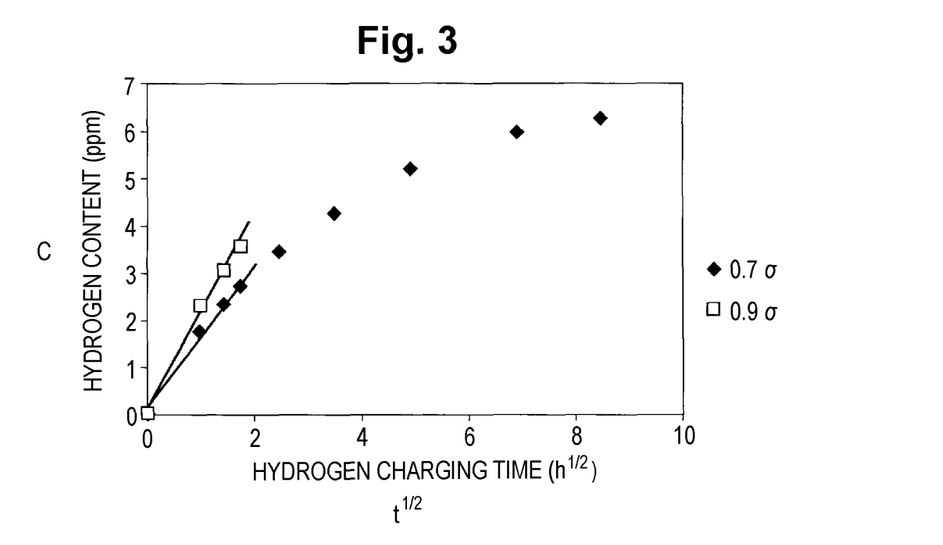
FIG. 3 is a diagram showing hydrogen penetration behavior $0.7\sigma_b$ and $0.9\sigma_b$ when hydrogen charging time is raised to the one-half power.

Next, the ratio calculation unit 13 reads the first measurement data and second measurement data out of the storage unit 3, plots the respective hydrogen penetration behaviors at $0.7\sigma_b$ and $0.9\sigma_b$ on a graph whose ordinate represents the hydrogen content C and whose abscissa represents the one-half power of the hydrogen charging time t used for measurement. The graph obtained by plotting the hydrogen content C against the one-half power of the hydrogen charging time t is shown in FIG. 3.

Next, using the generated graph, the ratio calculation unit 13 calculates the slopes (increases in the hydrogen content per predetermined time) of respective straight lines passing through plot points in the initial stage of diffusion. From the graph of FIG. 3, in the initial stage of diffusion, a slope $A_{0.7\sigma}$ under the stress condition in which the steel does not undergo hydrogen embrittlement fracture and a slope $A_{0.9\sigma}$ under the stress condition in which the steel undergoes hydrogen embrittlement fracture are given by Formula (2) and Formula (3), respectively.

Formula 2

$$A_{0.7\sigma} = 1.57 \quad (2)$$

Formula 3

$$A_{0.9\sigma} = 2.06 \quad (3)$$

Subsequently, the ratio calculation unit 13 calculates a ratio between the slopes of the two straight lines. From Formula (2) and Formula (3), the ratio of the slope $A_{0.9\sigma}$ to the slope $A_{0.7\sigma}$ is given by Formula (4).

Formula 4

$$\frac{A_{0.9\sigma}}{A_{0.7\sigma}} \cong 1.31 \quad (4)$$

Step 4;

In step 4, the saturated hydrogen content under the stress condition in which the steel does not undergo hydrogen embrittlement fracture is multiplied by the slope ratio found in step 3, and thereby the saturated hydrogen content under the stress condition in which the steel undergoes hydrogen embrittlement fracture is estimated. Step 4 will be described concretely below.

First, the saturated hydrogen content calculation unit 14 reads Formula (1) out of the storage unit 3. If it is assumed that under either of the stress condition in which the steel does not undergo hydrogen embrittlement fracture and the stress condition in which the steel undergoes hydrogen embrittlement fracture, the hydrogen diffusion coefficient D of the steel is constant, from Formula (1), the slope $A_{0.7\sigma}$ and slope $A_{0.9\sigma}$ are given by Formula (5) and Formula (6), respectively.

Formula 5

$$A_{0.7\sigma} = \frac{4}{a}\left(\frac{D}{\pi}\right)^{1/2} \cdot C_{s0.7\sigma} \quad (5)$$

Formula 6

$$A_{0.9\sigma} = \frac{4}{a}\left(\frac{D}{\pi}\right)^{1/2} \cdot C_{s0.9\sigma} \quad (6)$$

$C_{s0.7\sigma}$ is saturated hydrogen content at a load stress of $0.7\sigma_b$. $C_{s0.9\sigma}$ is saturated hydrogen content at a load stress of $0.9\sigma_b$. From Formula (5) and Formula (6), the saturated hydrogen content $C_{s0.9\sigma}$ is given by Formula (7).

Formula 7

$$C_{s0.9\sigma} = \frac{A_{0.9\sigma}}{A_{0.7\sigma}} C_{s0.7\sigma} \quad (7)$$

Formula (7) is the formula, described at the beginning of step 4, whereby "the saturated hydrogen content under the stress condition in which the steel does not undergo hydrogen embrittlement fracture is multiplied by the slope ratio found in step 3." According to Formula (7), by multiplying "the saturated hydrogen content $C_{s0.7\sigma}$" by "the ratio of the slope $A_{0.9\sigma}$ to the slope $A_{0.7\sigma}$" given by Formula (4), the saturated hydrogen content calculation unit 14 calculates the saturated hydrogen content $C_{s0.9\sigma}$ and outputs the saturated hydrogen content $C_{s0.9\sigma}$ to the display unit 5. This makes it possible to easily and simply estimate the saturated hydrogen content of steel under the stress condition in which hydrogen embrittlement fracture occurs. In the measurement according to the present embodiment, since saturated hydrogen content $C_{s0.7\sigma}$ is 6.40 ppm from FIG. 1, the saturated hydrogen content $C_{s0.9\sigma}$ is as given by Formula (8).

Formula 8

$$C_{s0.9\sigma} = 1.31 \cdot 6.40 \approx 8.38 \text{ (ppm)} \quad (8)$$

Step 5;

In step 5, since it is thought that the hydrogen in steel penetrates inside the steel by diffusion as described at the beginning of step 3, a hydrogen diffusion coefficient is calculated based on the variation, with time, of hydrogen content in the steel on assumption that hydrogen diffuses in the steel, and hydrogen penetration behavior data (the variation of hydrogen content with time) on the steel under the stress condition in which hydrogen embrittlement fracture occurs is calculated using a diffusion equation based on the calculated hydrogen diffusion coefficient. Step 5 will be described concretely below.

First, the hydrogen penetration behavior estimation unit 15 calculates the hydrogen diffusion coefficient D by substituting a=3.5 mm, $A_{0.9\sigma}$=2.06, and $C_{s0.9\sigma}$=8.38 ppm into Formula (6). As a result, the hydrogen diffusion coefficient D is given by Formula (9).

Formula 9

$$D \approx 1.45 \times 10^{-1} \text{ (mm}^2\text{/h)} \quad (9)$$

Figure 4:
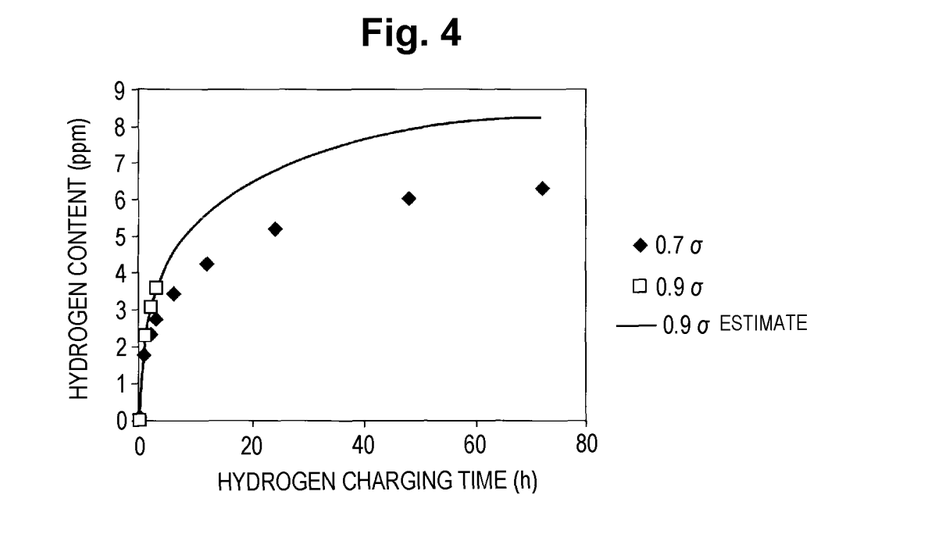
FIG. 4 is a diagram showing estimated hydrogen penetration behavior at $0.9\sigma_b$.

Next, using the hydrogen diffusion coefficient D of Formula (9) and the saturated hydrogen content $C_{s0.9\sigma}$ of Formula (7) or Formula (8) and using a diffusion equation capable of using an existing hydrogen diffusion coefficient and saturated hydrogen content as variables, the hydrogen penetration behavior estimation unit 15 calculates hydrogen penetration behavior data on the steel at a load stress of $0.9\sigma_b$, for example, by a common numerical calculation method based on a difference method, and outputs the hydrogen penetration behavior data to the display unit 5. The hydrogen penetration behavior data on the steel estimated by the calculation is the $0.9\sigma$ estimate shown in FIG. 4.

Thus, according to the present embodiment, since the hydrogen penetration behavior estimation device 1 includes the first measurement data input unit 11 adapted to input first measurement data concerning variation of hydrogen content with time up until hydrogen content in steel-to-be-estimated reaches saturation when measurements are taken by applying such stress to the steel that no fracture due to hydrogen embrittlement occurs; the second measurement data input unit 12 adapted to input second measurement data concerning variation of hydrogen content in the steel-to-be-estimated with time up until the steel fractures when measurements are taken by applying such stress to the steel that fracture due to hydrogen embrittlement occurs; the ratio calculation unit 13 adapted to read the first measurement data and the second measurement data out of the storage unit 3, calculate increases in hydrogen contents in an initial stage of measurement using the first measurement data and the second measurement data, respectively, and calculate a ratio of the increase in the hydrogen content according to the second measurement data to the increase in the hydrogen content according to the first measurement data; and the saturated hydrogen content calculation unit 14 adapted to multiply saturated hydrogen content based on the first measurement data by the ratio and designate a resulting product as saturated hydrogen content of the steel-to-be-estimated, the saturated hydrogen content being reached upon application of such stress that fracture due to hydrogen embrittlement occurs, hydrogen penetration behavior in high-strength steel when load stress on the steel is equal to or higher than a threshold stress can be estimated. That is, under the stress condition in which hydrogen embrittlement fracture occurs, hydrogen penetration behavior in high-strength steel can be estimated easily and simply while this has been difficult before.

Figure 5:
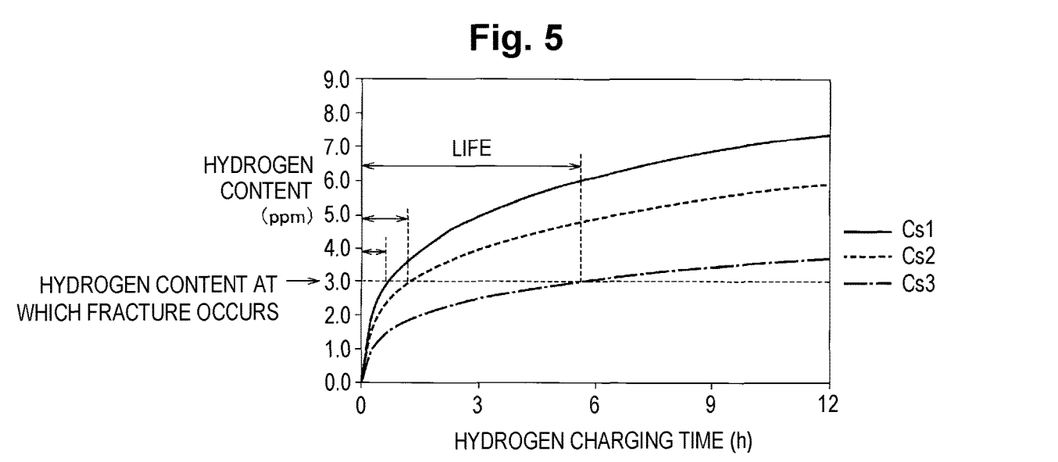
FIG. 5 is a diagram showing a relationship between saturated hydrogen content and steel life.

When a same material is used, it is thought that the lower the hydrogen content penetrating into the steel, the longer the time until fracture occurs. Thus, if hydrogen penetration behavior can be estimated accurately under the stress condition in which hydrogen embrittlement fracture occurs, the reduction of penetrating hydrogen content can be established as one of development guidelines for steel materials with long hydrogen embrittlement fracture life. If the hydrogen content that causes fracture to occur as well as the hydrogen diffusion coefficient are constant, because the lower the saturated hydrogen content $C_s$ ($C_s1>C_s2>C_s3$), the longer the life of the steel in relation to hydrogen embrittlement fracture as shown in FIG. 5, the reduction of the saturated hydrogen content $C_s$ can be established as a development guideline in developing materials with long steel life in relation to hydrogen embrittlement fracture.

Finally, the hydrogen penetration behavior estimation device 1 described in the present embodiment can be implemented by a computer and programs, where the programs can be recorded on a recording medium or provided via a communications network.

REFERENCE SIGNS LIST

1 Hydrogen penetration behavior estimation device
11 First measurement data input unit
12 Second measurement data input unit
13 Ratio calculation unit
14 Saturated hydrogen content calculation unit
15 Hydrogen penetration behavior estimation unit
3 Storage unit
5 Display unit

The invention claimed is:

1. A hydrogen penetration behavior estimation method for estimating penetration behavior of hydrogen that penetrates steel, the method making a computer carry out:
   a first step of inputting first measurement data concerning variation of hydrogen content with time up until hydrogen content in steel-to-be-estimated reaches saturation when measurements are taken by applying such stress to the steel that no fracture due to hydrogen embrittlement occurs;
   a second step of inputting second measurement data concerning variation of hydrogen content in the steel-to-be-estimated with time up until the steel fractures when measurements are taken by applying such stress to the steel that fracture due to hydrogen embrittlement occurs;
   a third step of reading the first measurement data and the second measurement data out of a storage unit, calculating increases in hydrogen contents in an initial stage of measurement using the first measurement data and the second measurement data, respectively, and calculating a ratio of the increase in the hydrogen content according to the second measurement data to the increase in the hydrogen content according to the first measurement data; and
   a fourth step of multiplying saturated hydrogen content based on the first measurement data by the ratio and designating a resulting product as saturated hydrogen content of the steel-to-be-estimated, the saturated hydrogen content being reached upon application of such stress that fracture due to hydrogen embrittlement occurs.

2. The hydrogen penetration behavior estimation method according to claim 1, wherein the computer is further made to carry out a fifth step of calculating a hydrogen diffusion coefficient of the steel-to-be-estimated based on the variation, with time, of the hydrogen content in the steel on assumption that hydrogen diffuses in the steel, and calculating penetration behavior data concerning the hydrogen content in the steel-to-be-estimated upon application of such stress that fracture due to hydrogen embrittlement occurs, using a diffusion equation based on the hydrogen diffusion coefficient.

3. The hydrogen penetration behavior estimation method according to claim 2, wherein the third step includes plotting the first measurement data and the second measurement data on a graph whose ordinate represents hydrogen content and whose abscissa represents one-half power of hydrogen charging time used for measurement, and calculating the ratio using slopes of respective straight lines passing through plot points in the initial stage of measurement.

4. The hydrogen penetration behavior estimation method according to claim 1, wherein the third step includes plotting the first measurement data and the second measurement data on a graph whose ordinate represents hydrogen content and whose abscissa represents one-half power of hydrogen charging time used for measurement, and calculating the ratio using slopes of respective straight lines passing through plot points in the initial stage of measurement.

5. A hydrogen penetration behavior estimation device that estimates penetration behavior of hydrogen that penetrates steel, the hydrogen penetration behavior estimation device comprising:
   a first measurement data input unit adapted to input first measurement data concerning variation of hydrogen content with time up until hydrogen content in steel-to-be-estimated reaches saturation when measurements are taken by applying such stress to the steel that no fracture due to hydrogen embrittlement occurs;
   a second measurement data input unit adapted to input second measurement data concerning variation of hydrogen content in the steel-to-be-estimated with time up until the steel fractures when measurements are taken by applying such stress to the steel that fracture due to hydrogen embrittlement occurs;
   a ratio calculation unit adapted to read the first measurement data and the second measurement data out of a storage unit, calculate increases in hydrogen contents in an initial stage of measurement using the first measurement data and the second measurement data, respectively, and calculate a ratio of the increase in the hydrogen content according to the second measurement data to the increase in the hydrogen content according to the first measurement data; and
   a saturated hydrogen content calculation unit adapted to multiply saturated hydrogen content based on the first measurement data by the ratio and designate a resulting product as saturated hydrogen content of the steel-to-be-estimated, the saturated hydrogen content being reached upon application of such stress that fracture due to hydrogen embrittlement occurs.

6. The hydrogen penetration behavior estimation device according to claim 5, further comprising a hydrogen penetration behavior estimation unit adapted to calculate a hydrogen diffusion coefficient of the steel-to-be-estimated based on the variation, with time, of hydrogen content in the steel on assumption that hydrogen diffuses in the steel, and calculate penetration behavior data concerning the hydrogen content in the steel-to-be-estimated upon application of such stress that fracture due to hydrogen embrittlement occurs, using a diffusion equation based on the hydrogen diffusion coefficient.

7. The hydrogen penetration behavior estimation device according to claim 6, wherein the ratio calculation unit plots the first measurement data and the second measurement data on a graph whose ordinate represents hydrogen content and whose abscissa represents one-half power of hydrogen charging time used for measurement, and calculates the ratio using slopes of respective straight lines passing through plot points in the initial stage of measurement.

8. A hydrogen penetration behavior estimation program configured to make a computer function as the hydrogen penetration behavior estimation device according to claim 6.

9. The hydrogen penetration behavior estimation device according to claim 5, wherein the ratio calculation unit plots the first measurement data and the second measurement data on a graph whose ordinate represents hydrogen content and whose abscissa represents one-half power of hydrogen charging time used for measurement, and calculates the ratio using slopes of respective straight lines passing through plot points in the initial stage of measurement.

10. A hydrogen penetration behavior estimation program configured to make a computer function as the hydrogen penetration behavior estimation device according to claim 9.

11. A hydrogen penetration behavior estimation program configured to make a computer function as the hydrogen penetration behavior estimation device according to claim 5.

\* \* \* \* \*